United States Patent [19]

Vrieland

[11] Patent Number: 4,859,786
[45] Date of Patent: Aug. 22, 1989

[54] OLEFIN OXIDATION CATALYST OF UNSUPPORTED SILVER CONTAINING LOW LEVELS OF MAGNESIUM

[75] Inventor: G. Edwin Vrieland, Midland, Mich.

[73] Assignee: The Dow Chemical Company, Midland, Mich.

[21] Appl. No.: 27,580

[22] Filed: Mar. 18, 1987

Related U.S. Application Data

[63] Continuation of Ser. No. 761,112, Jul. 31, 1985, abandoned.

[51] Int. Cl.⁴ ............................................ C07D 301/06
[52] U.S. Cl. ..................................................... 549/537
[58] Field of Search ........................................ 549/537

[56] References Cited

U.S. PATENT DOCUMENTS 2,562,858  7/1951  Cambron et al. .................... 549/537
2,686,762  8/1954  Tollefson et al. .................... 549/537
3,959,316  5/1976  Piccinini et al. ..................... 549/537
4,007,135  2/1977  Hayden et al. ...................... 549/537

FOREIGN PATENT DOCUMENTS 1109658  6/1961  Fed. Rep. of Germany ...... 549/537
1421189  6/1980  German Democratic Rep. .................................... 549/537

Primary Examiner—Richard L. Raymond
Assistant Examiner—Mark W. Russell
Attorney, Agent, or Firm—Marie F. Zuckerman; Paul M. Bork

[57] ABSTRACT

Olefins such as propylene can be oxidized to their epoxides by contacting gaseous olefin with oxygen in the presence of an unsupported silver catalyst. This catalyst is promoted with 30 to 1300 ppm (weight) magnesium relative to the silver.

13 Claims, No Drawings

OLEFIN OXIDATION CATALYST OF UNSUPPORTED SILVER CONTAINING LOW LEVELS OF MAGNESIUM

This is a continuation of application Ser. No. 761,112, filed July 31, 1985, now abandoned.

BACKGROUND OF THE INVENTION

This invention relates to silver catalysts and their use in olefin epoxidation. More particularly, it relates to silver catalysts containing low levels of magnesium promoter.

Epoxides are reaction intermediates useful in production of numerous polymers, solvents and resins.

Direct oxidation of olefins with air or with gases containing molecular oxygen can be carried out by contacting the olefin vapor with the molecular oxygen in the presence of a silver-containing catalyst. The reaction is generally performed under conditions such that the olefin is in the vapor state. Part of the olefin is disadvantageously oxidized into carbon dioxide and water. It is desirable that the reaction be as selective as possible to the epoxide. A second consideration is the reactivity of the catalyst. The reactivity should be sufficient to allow an acceptable rate of production. Thus, an important feature of a catalyst is a good combination of selectivity and reactivity under reaction conditions. Generally, catalysts are supported to increase their performance and effective surface area.

It is known to use a supported silver catalyst with co-promoters, one of which is taught may be magnesium at 0.1 to 50 atomic percent based on silver. See U.S. Pat. No. 4,007,135.

U.S. Pat. 4,242,235 teaches that ethylene epoxidation can be catalyzed with a supported silver catalyst containing 0 to 2 weight percent (based on total catalyst weight) magnesium promoter.

U.S. Pat. No. 4,400,308 teaches use of a supported silver catalyst containing 0.05 to 0.5 weight percent (based on total catalyst weight) alkaline earth promoter to convert alkenes to epoxides.

While known catalysts are sufficient to effectively oxidize ethylene to ethylene oxide, they generally have a low selectivity when epoxidation of propylene is attempted. It is desirable to have a catalyst having better selectivity and activity for the epoxidation of propylene to propylene oxide.

SUMMARY OF THE INVENTION

In one aspect, the present invention is a process for converting an olefin to an epoxide which process comprises contacting an olefin with oxygen in the presence of an unsupported silver catalyst containing an amount of magnesium promoter less than about 0.1 weight percent based on the silver but sufficient to increase the selectivity to the epoxide formed.

In another aspect, the invention is the aforementioned unsupported silver catalyst.

It is surprising that such low levels of magnesium promoter will enhance the performance of an unsupported silver epoxidation catalyst above that of both the unpromoted silver epoxidation catalyst and the catalyst with higher levels of magnesium promoter.

DETAILED DISCUSSION OF ILLUSTRATIVE EMBODIMENTS

The olefins employed in the process of this invention are any which are readily oxidized to epoxides in the presence of silver catalysts. Examples of such olefins are ethylene, propyplene, 1,2-butylene, 2,3-butylene, 1,2-pentene and 2,3-pentene, with ethylene and propylene being preferred and propylene being most preferred.

The oxygen is employed in the form of any gas containing molecular oxygen which is suitably employed in conventional vapor phase oxidation of olefins, e.g., air.

The unsupported silver catalyst comprises (1) silver including compounds of silver in a form which is catalytically active for the oxidation of olefins to epoxides and (2) magnesium in a form which promotes said oxidation to a selectivity of greater than that produced by the silver in the absence of the magnesium. The weight ratio of magnesium to silver is less than about 0.001:1, preferably less than about 0.0005:1, and most preferably less than about 0.000441:1. The weight ratio of magnesium to silver is preferably more than about 0.00003:1, more preferably more than about 0.000035:1 and most preferably more than about 0.000043:1.

While the catalyst can be made in any operative method, preferred are catalysts made by drying and reducing precipitated magnesium ions and silver ions. These ions can be prepared by dissolving salts such as $AgNO_3$, $Mg(NO_3)_2$, $Mg(OH)_2$ and the like in water. More preferred catalysts are those which have been precipitated from water solutions. Most preferred are those which have been coprecipitated from water solutions. The catalyst can be prepared and precipitated in ordinary laboratory glassware. The catalyst precipitates in a particulate powder. The particles can be dried in an inert atmosphere such as nitrogen to a free-flowing powder with the largest particles perceptible to an unaided eye. The particles can then be reduced to form the catalyst by techniques such as exposure to an atmosphere composed of 10 mole percent hydrogen/90 mole percent nitrogen for 18 hours at a temperature of 60° C. then 2 hours at a temperature of 130° C. Typically, the catalyst has particles between about 0.5 mm and about 0.1 mm.

For the purpose of this patent, selectivity is the percentage of consumed olefin that reacts to form an epoxide. Conversion is the percentage of olefin in the feed that reacts.

Preferred are catalysts that yield selectivities to epoxide of at least about 34 percent, while the conversion of olefin is at least about 0.6 percent.

The catalyst is contacted with olefin and oxygen under conditions such that the epoxide of the olefin is formed. The olefin and oxygen are present in an amount sufficient to allow formation of the epoxide. Preferably, the mole ratio of oxygen to olefin is above about 1:20, more preferably above about 1:10. The mole ratio of oxygen to olefin is preferably below about 2:3, more preferably below about 2.5. The most preferable mole ratio is 1:4. The olefin is preferably saturated with water vapor. This can be accomplished by bubbling the olefin through liquid water. Small amounts of a usual inhibitor, e.g., 1 to 5 ppm of 1,2-dichloroethane, may be used when the olefin is ethylene.

The pressure and temperature should be adjusted to achieve optimal results for each catalyst and feed mixture. the pressure may be subatmospheric through superatmospheric with superatmospheric pressures preferred. It is more preferred to use pressures from about 150 psig to about 200 psig. It is most preferable to use pressures from about 180 psig through about 200 psig.

The reaction can occur at any operable temperature upon contacting the catalyst with the reactants. Preferred is contact with a catalyst heated to a temperature above about 110° C., more preferred is contact with a catalyst heated to a temperature above about 130° C., and most preferred is contact with a catalyst heated to a temperature above about 140° C. Preferred is contact with a catalyst heated to a temperature below about 250° C., more preferred below about 170° C., most preferred below about 150° C.

The catalyst is present in an amount sufficient to catalyze the formation of epoxide. Preferably, the catalyst is present in an amount greater than about $5 \times 10^6$ g catalyst per cubic meter per second reactant flow rate (g-sec/m$^3$), more preferably greater than about $10 \times 10^6$ g-sec/m$^3$ and even more preferably greater than about $12 \times 10^6$ g-sec/m$^3$. Preferably, the catalyst is present in an amount less than about $50 \times 10^6$ g-sec/m$^3$, more preferably less than about $25 \times 10^6$ g-sec/m$^3$ and even more preferably less than about $20 \times 10^6$ g-sec/m$^3$. Most preferably, the catalyst is present in an amount of about $16 \times 10^6$ g-sec/m$^3$.

The reactant's residence time in the catalyst zone of the reactor (residence time) is sufficient to allow for some epoxide formation. Preferably, the residence time is larger than about 5 seconds, more preferably larger than about 10 seconds, even more preferably larger than about 12 seconds; the residence time is preferably less than about 100 seconds, more preferably less than about 50 seconds, even more preferably less than about 25 seconds. Most preferably, the residence time is about 20 seconds.

The reactants can be contacted with the catalyst in any suitable reactor. Preferred are tubular stainless steel reactors. Generally, plugs of glass wool are used to keep the catalyst in the reactor. The feed is preferably preheated to the reaction temperature.

The invention is further illustrated by the following illustrative embodiments.

Illustrative Embodiment 1

A first water solution containing 17.0 g (0.100 mole) of AgNO$_3$ and 2.56 g (0.010 mole) of Mg(NO$_3$)$_2$.6H$_2$O to make 1 liter of solution is combined with a second water solution containing 25 g (0.298 moles) of NaHCO$_3$ to make 1 liter of solution. The combination is made by pumping the first water solution into the stirred second water solution at a rate of 0.020 liter/minute. A yellow precipitate forms. The combined solutions are filtered. The yellow precipitate is washed three times with 0.300liter portions of water. The washed precipitate is dried (at room temperature) overnight (18 hours). The dried prcipitate is heated to 60° C. in a nitrogen atmosphere for about 1 hour, then overnight (18 hours) in a 10 mole percent hydrogen/90 mole percent nitrogen atmosphere at a temperature of about 60° C. The temperature is then raised to 130° C. for 1-2 hours to produce the gray catalyst, which is a free-flowing powder.

Illustrative Embodiment 2

A first water solution containing 20 g (0.118 moles) of AgNO$_3$ to make 1 liter of solution is added to 1 liter of a second solution of 0.3 normal NaOH saturated with Mg(OH)$_2$ at 20° C. The resulting black precipitate is washed and heated as in Illustrative Embodiment 1, to produce a free-flowing powder.

Illustrative Embodiments 3–5

Catalysts are prepared by the method of Illustrative Embodiment 1 except the amount of magnesium relative to silver in the solutions is varied from a molar ratio of 0.1 to 0.6.

Illustrative Embodiments 6–8

Catalysts are prepared as in Illustrative Embodiment 1 except no Mg(NO$_3$)$_2$ is in the first water solution. After filtering and washing but before drying, the washed precipitate is impregnated with water solutions of varying concentrations of Mg(NO$_3$)$_2$. The impregnated precipitates are dried and reduced as described in Illustrative Embodiment 1.

Illustrative Embodiments 9–16

Catalysts (4 g) prepared by the methods of preceding Illustrative Embodiments are placed in a 0.008 M inside diameter heated stainless steel block approximately 7 inches long. Glass wool plugs are placed on either side of the catalyst to keep the catalyst in the reactor. Preheated reactants (68 mole percent propylene and 32 mole percent oxygen unless otherwise noted) are fed to the reactor at 15 cubic centimeters per minute (cc/m) and the products are detected by an on-stream gas chromatograph. The results are reported in Table I.

TABLE I

| Illustrative Embodiment | Catalyst From Illustrative Embodiment | Mg In Catalyst (ppm) | Reaction Temperature (°C.) | Conversion of Propylene (Percent) | Selectivity To Propylene Oxide (Percent) |
|---|---|---|---|---|---|
| 9 | 1[1] | UNM[2] | 150 | 0.7 | 37.9 |
| 10 | 2 | UNM[3] | 130 | 1.2 | 35.2 |
| 11 | 3 | 43 | 140 | 1.5 | 34.1 |
| 12 | 4 | 48 | 140 | 1.5 | 40.4 |
| 13 | 5 | 97 | 140 | 0.6 | 41.6 |
| 14 | 6 | 81 | 140 | 1.07 | 35.9 |
| 15 | 7 | 188 | 140 | 1.32 | 36.0 |
| 16 | 8 | 441 | 140 | 0.93 | 36.5 |

Notes:
UNM = unmeasured
[1]Feed: 74 molar percent propylene, 26 molar percent oxygen
[2]0.1 molar ratio of Mg to Ag is added to solutions in making the catalyst
[3]NaOH solution is saturated with Mg(OH)$_2$ in making the catalyst Comparative Embodiment 1

A catalyst is prepared by the method of Illustrative Embodiment 6, except no Mg(NO$_3$)$_2$ is impregnated into the precipitate. This catalyst is the precipitated silver without any added magnesium.

Comparative Embodiments 2 and 3

The catalyst is prepared by the method of Illustrative Embodiment 1, except a larger amount of magnesium relative to silver is added. The results are reported in Table II.

TABLE II

| Comparative Embodiment | Mg In Catalyst (ppm) | Temperature Of Reaction (°C.) | Conversion Of Propylene (Percent) | Selectivity To Propylene Oxide (Percent) |
| --- | --- | --- | --- | --- |
| 1 | 24 | 140 | 0.92 | 18.7 |
| 2 | 2,900 | 140 | 0.96 | 7.9 |
| 3 | 1,900 | 140 | 0.43 | 5.6 |

Comparing Table I with Table II shows that a silver catalyst containing small amounts of magnesium has higher selectivities to propylene oxide while retaining reasonable conversions of propylene than either the unpromoted catalyst or the catalyst promoted with magnesium at conventional levels.

Illustrative Embodiment 17

A heated stainless steel reactor (inside diameter of 0.008 M) is charged with 4 g of a catalyst prepared by the method of Illustrative Embodiment 4 which contains 48 ppm magnesium. A preheated feed of 85 mole percent ethylene and 15 mole percent oxygen is contacted with the catalyst at a rate of 15 cc/m at a temperature of 150° C. The conversion is 1.9 percent with a selectivity of 84.4 percent to ethylene oxide. After 50 hours of reaction, the conversion is 1.2 percent and the selectivity is 86 percent.

This illustrative embodiment demonstrates the catalyst reactivity after the catalyst has been used.

I claim:

1. A process for converting an olefin to an epoxide which process comprises contacting an olefin with oxygen in the presence of an unsupported silver catalyst containing a amount of magnesium promoter, such that the weight ratio of magnesium to silver is less than about 0.001:1 but sufficient to increase the selectivity to the epoxide formed to at least about 34 percent while the conversion of olefin is at least about 0.6 percent; said olefin being selected from the group consisting of propylene, 1,2 butylene, 2,3-butylene, 1,2-pentene and 2,3-pentene.

2. The process of claim 1 in which the weight ratio of magnesium to silver is between about 0.0005:1 and about 0.00003:1.

3. The process of claim 2 in which the weight ratio of magnesium to silver is between about 0.000441:1 and about 0.000043:1.

4. The process of claim 1 in which the contact occurs at a pressure between about 150 psig and about 200 psig.

5. The process of claim 4 in which the pressure is between about 180 psig and about 200 psig.

6. The process of claim 4 in which the temperature of the contacting oxygen and olefin is between about 110° C. and about 250° C.

7. The process of claim 1 in which the catalyst is present in an amount between about $5 \times 10^6$ g-sec/m$^3$ and about $50 \times 10^6$ g-sec/m$^3$.

8. The process of claim 1 in which the reactant residence time is between about 5 seconds and about 100 seconds.

9. The process of claim 1 in which the olefin feed is about saturated with water.

10. A process for converting propylene to propylene oxide, which process comprises contacting propylene with oxygen in the presence of an unsupported silver catalyst containing an amount of magnesium promoter, such that the weight ratio of magnesium to silver is less than about 0.001:1 but sufficient to increase the selectivity to the epoxide formed to at least about 34 percent while the conversion of olefin is at least about 0.6 percent.

11. The process of claim 1 wherein the oxygen and olefin are employed in an oxygen/olefin mole ratio above about 1:20 and below about 2:3.

12. The process of claim 6 wherein the contacting is conducted at a temperature above about 130° C. and below about 170° C.

13. The process of claim 12 wherein the temperature is above about 140° C. and below about 150° C.

* * * * *